(12) United States Patent
Kamstra et al.

(10) Patent No.: US 11,800,843 B2
(45) Date of Patent: Oct. 31, 2023

(54) POWDERY MILDEW RESISTANT ROSE

(71) Applicant: Dümmen Group B.V., De Lier (NL)

(72) Inventors: Silvan Adelmar Kamstra, De Lier (NL); Camillo Bérénos, De Lier (NL)

(73) Assignee: Dümmen Group B.V., De Lier (NL)

( * ) Notice: Subject to any disclaimer, the term of this patent is extended or adjusted under 35 U.S.C. 154(b) by 411 days.

(21) Appl. No.: 16/629,808

(22) PCT Filed: Jul. 3, 2018

(86) PCT No.: PCT/EP2018/067908
§ 371 (c)(1),
(2) Date: Jan. 9, 2020

(87) PCT Pub. No.: WO2019/011718
PCT Pub. Date: Jan. 17, 2019

(65) Prior Publication Data
US 2022/0228162 A1    Jul. 21, 2022

(30) Foreign Application Priority Data

Jul. 10, 2017  (NL) .................................... 2019209

(51) Int. Cl.
*C12N 15/82* (2006.01)
*C12Q 1/68* (2018.01)

(52) U.S. Cl.
CPC .............................. *C12N 15/8282* (2013.01)

(58) Field of Classification Search
None
See application file for complete search history.

(56) References Cited

FOREIGN PATENT DOCUMENTS

JP        S57202230 A     12/1982

OTHER PUBLICATIONS

Koning-Boucoiran et al. Acta Hort. (2009) 836:137-142.*
Li et al. Planta (2003) 218:226-232.*
Linde et al., "Rpp1, A Dominant Gene Providing Race-Specific Resistance to Rose Powdery Mildew (*Podosphaera pannosa*): Molecular Mapping, SCAR Development and Confirmation of Disease Resistance Data", Theor Appl Genet, 2004, pp. 1261-1266, vol. 109.
Linde et al., "Powdery Mildew Resistance in Roses: QTL Mapping in Different Environments Using Selective Genotyping", Theor Appl Genet, 2006, pp. 1081-1092, vol. 113.
Moghaddam et al., "Construction of a Genetic Linkage Map with SSR, AFLP and Morphological Markers to Locate QTLs Controlling Pathotype-Specific Powdery Mildew Resistance in Diploid Roses", Euphytica, 2012, pp. 413-427, vol. 184.
Qui et al., "Expression Pattern Analysis of Four Mlo Genes from Rose", J. Amer. Soc. Hort. Sci., 2015, pp. 333-338, vol. 140, No. 4.
Xu et al., "Cloning of Two Classes of PR Genes and the Development of SNAP Markers for Powdery Mildew Resistance Loci in Chestnut Rose (*Rosa roxburghii tratt*)", Mol Breeding, 2007, pp. 179-191, vol. 19.
Yan et al., "Assessment of Partial Resistance to Powdery Mildew (*Podosphaera pannosa*) in a Tetrapioid Rose Population Using a Spore-Suspension Inoculation Method", European Journal of Plant Pathology, 2006, pp. 301-308, vol. 114.
Homma et al., "Effect of Continuous Glucose Treatment on Flower Longevity in Cut Roses", Bulletin of the Shizuoka Research Institute of Agriculture and Forestry, 2014, pp. 1-11, vol. 7, English-language Abstract.

* cited by examiner

*Primary Examiner* — Medina A Ibrahim
(74) *Attorney, Agent, or Firm* — The Webb Law Firm

(57) ABSTRACT

Provided herein are rose plants such as cut roses, garden roses and pot roses having at least two genes providing resistance to a pathogen causing powdery mildew. Specifically, provided herein are rose plants resistant to the powdery mildew causing pathogen *Podosphaera pannosa* also known as *Sphaerotheca pannosa* var. *rosae*. Also provided herein are methods for selecting the present powdery mildew rose plants. The present rose plants are characterized by including in their nuclear genome at least one nucleotide sequence represented by SEQ ID No. 1 and at least one nucleotide sequence represented by SEQ ID No. 2 wherein the combined presence of SEQ ID No. 1 and SEQ ID No. 2 provides powdery mildew resistance.

Figure 1:
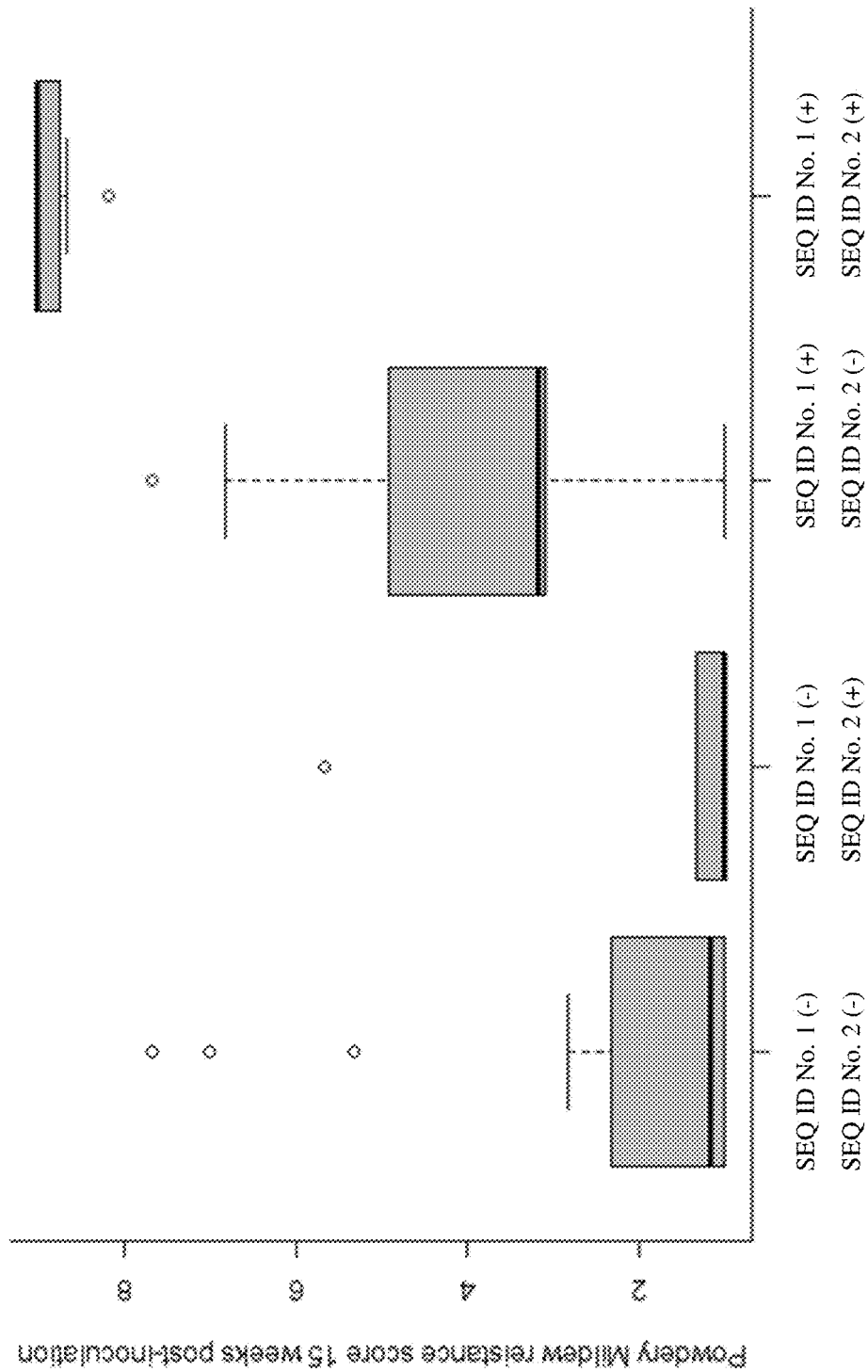

9 Claims, 2 Drawing Sheets
Specification includes a Sequence Listing.

SEQUENCE LISTING

<160> NUMBER OF SEQ ID NOS: 2

<210> SEQ ID NO 1
<211> LENGTH: 52
<212> TYPE: DNA
<213> ORGANISM: Rosa

<400> SEQUENCE: 1
tttgttcatt ataaactcat tcctcgcttc ctcaaccttc tctgaaacga cc          52

<210> SEQ ID NO 2
<211> LENGTH: 50
<212> TYPE: DNA
<213> ORGANISM: Rosa

<400> SEQUENCE: 2
ggcttttcgc cctgcgtctt gctctccaaa aactcactac taatttgtca             50

POWDERY MILDEW RESISTANT ROSE

CROSS-REFERENCE TO RELATED APPLICATIONS

This application is the U.S. national phase of International Application No. PCT/EP2018/067908 filed Jul. 3, 2018, and claims priority to The Netherlands Patent Application No. 2019209 filed Jul. 10, 2017, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1908859_ST25.txt. The size of the text file is 547 bytes, and the text file was created on Dec. 10, 2019.

DESCRIPTION

The present invention relates to rose plants such as cut roses, garden roses, pot roses and rose rootstocks comprising at least two genes providing resistance to a pathogen causing powdery mildew. Specifically, the present invention relates to rose plants resistant to the powdery mildew causing pathogen *Podosphaera pannosa* also known as *Sphaerotheca pannosa* var. rosae. The present invention further relates to methods for selecting the present powdery mildew rose plants.

Powdery mildew (PM) is a major foliar disease in cut, pot and garden rose and is caused by the obligate biotrophic ascomycete *Podosphaera pannosa* also known as *Sphaerotheca pannosa*. Symptoms of a powdery mildew infection include retarded growth of the plants and leaf deformation due to the formation of white powdery conidia that appear on plant surfaces such as leaves, flowers, stems and buds. No official figures exist for production losses in rose as a result of powdery mildew, but controlling powdery mildew in three major greenhouse crops cucumber, tomato and rose costs C$ 6,000/ha in Canada.

Powdery mildew disease can be controlled by chemicals, but the use of fungicides is expensive, laborious and damaging to the environment. Increasingly strict regulations on the use of chemicals in horticulture are being put in place by governments throughout the world, which in combination with the aforementioned factors, means that developing powdery mildew resistant rose varieties pivotal in managing and avoiding financial loss due to powdery mildew outbreaks.

While *Podosphaera pannosa* is able to infect a broad range of hosts, including *Prunus cerasus* and *Prunus avium*, the interaction between *Podosphaera pannosa* and rose is characterized by a high degree of specificity. For instance, several pathotypes of the fungus were described half a century ago and more recently an assay examining the compatibility between 8 monoconidial isolates and 18 host genotypes revealed a high level of specificity and racial diversity.

Cut roses are susceptible to powdery mildew (PM). In order to breed for cut roses resistant to PM there is a need to identify resistance genes. Several publications have shown evidence for a genetic basis for powdery mildew resistance in the genus *Rosa*, with resistance ranging from qualitative to quantitative resistance. However, the commercially important cut roses (*Rosa hybrida*) are generally tetraploid and quantitative trait loci (QTL) for powdery mildew resistance have mostly been shown in other species or varieties than *Rosa hybrida*.

For instance, using a diploid *Rosa multiflora* hybrid BC1 population (n=117) created by crossing a resistant line (88/124-46) with a susceptible line (82/78-1) and backcrossing the F1 hybrid 95/13-90 with 82/78-1, it was found that the Rpp1 gene is a major effect gene on linkage group 3 conferring PM resistance until 10 days post-inoculation with a dominant monogenic mode of action. Using a different diploid *R. multiflora* hybrid F1 population (n=270) created by crossing a resistant line (95/13-39) with a susceptible line (Sp3 or 82/78-1) from the same open-pollinated breeding program which intended to introgress genes from tetraploid garden roses into *Rosa multiflora*, QTLs were mapped for resistance in six different environments. In total, 28 different QTLs were found on linkage groups 1, 2, 3, 4, 6 and 7, with a strong clustering of QTL on linkage groups 3 and 4, which altogether is indicative of a polygenic resistance mechanism. A substantial proportion of the observed phenotypic variance for resistance (31%) was inherited from the susceptible parent, and interestingly the aforementioned effect of the Rpp1 gene was not shown in this population.

In a diploid cross (n=90) between the rose cultivar "Yesterday" and *Rosa wichurana* 9 QTL for resistance until 10 days post-inoculation against 2 races were found on linkage groups 2, 3, 5 and 6, each explaining between 15% and 74% of the phenotypic variance. Of the 9 QTL, only one was detected using both races. While most of the resistance alleles originated from *Rosa wichurana*, both parents contributed to the variation in resistance.

The only example of resistance providing QTLs in tetraploid cut rose, stems from the K5 population, an F1 population which was created by crossing two cultivars: P540 and P867, both of which were only partially resistant. Two different fungal monospore isolates were used, and resistance was scored using three different disease scores: disease score 11 days post inoculation (dpi), latency period and rate of symptom development. For each of the three disease scores, between 16 and 28 markers, covering all 7 linkage groups, were shown to be associated with powdery mildew, although no exact statistical support is given. While a number of markers were associated with different disease scores, none of the markers were detected for both isolates. For each of the six combinations of isolate and disease score, multiple regressions were then performed using 4 or 5 of the most significant markers. Phenotypic variance explained by the multiple regressions ranged between 10.4 and 22.3% indicating that resistance in this cross is quantitative and controlled by multiple genes with only a minor effect each.

Thus, while several studies have published QTLs for powdery mildew resistance in rose, an overarching theme is that there is little consistency in and agreement among the published results. For instance, resistance ranged from monogenic to quantitative. Additionally, no QTLs were shared between studies, suggesting that there might be heterogeneity in genetic mechanisms underlying recognition of fungal proteins and thus powdery mildew resistance. In part this heterogeneity might be a result of the genetic diversity among and even within isolates which in combination with the hypothesized gene-for-gene model of interaction explains the locations and effect sizes of QTLs can depend on the isolate used.

Alternatively, the lack of confirmation questions the robustness of the conclusions drawn, either due to the often low sample size, low marker coverage, or a combination thereof. A diploid F1 population of *Rosa roxburghii* (cv. Guinong no. 6 x cv. Guinong no. 5) was evaluated under natural disease pressures, 4 resistance gene analogues (RGAs) that could not be assigned to a linkage group were associated with CRPM1, a major R locus, which was not assigned to a LG, explaining 72% of the phenotypic variation in powdery mildew resistance.

Mildew resistance locus (MLO) based resistance was first identified in barley (*Hordeum vulgare*), as a recessive allele providing durable resistance against all mildew (*Blumeria graminis* f. sp. *horde*) isolates. MLO-based resistance is not unique to barley as MLO orthologues have since been discovered in many other plant genera such as *Pisum, Arabidopsis and Solanum*, where loss of function mutations in MLO genes have been shown to lead to broad spectrum resistance to powdery mildew. The MLO protein family consists of 7 clades, and although widespread in land plants, the function of most MLO genes is unknown, and all MLO genes which have shown to be associated with powdery mildew resistance are found in Clade V. In apple (*Malus domestica*), a member of the Rosaceae family, out of 21 MLO genes only three MLO homologs, of which two belonged to Glade V, were upregulated after infection with powdery mildew. This suggests that detecting MLO homologs in itself does not suffice to identify a gene to be involved in powdery mildew resistance.

However, despite its durability, MLO-based resistance often has deleterious pleiotropic effects such as necrotic leaf spotting and reduced vigour, thus imposing barriers when designing a breeding strategy. In rose (diploid *Rosa multiflora* hybrids and tetraploid *Rosa hybrida* cv. Pariser Charme) four MLO genes, designated RhML01 to 4, have been identified based on their sequence homology to well-characterized sequences obtained in barley and *Arabidopsis*). Each gene harboured between two and six alleles, consisted of 15 exons, and total length of the coding sequence was in all cases approximately 1,700 bp. The MLO genes were distributed over several linkage groups, with rhMLO3 and rhMLO4 clustering together on LG1 (between 40 and 45 cM), rhMLO2 found on LG3(at ca. 35 cM) and rhMLO1 at round 60 cM found on LGS.

No loss of function mutants are currently known in rose, but all four MLO homologs were shown to belong to Glade V, the only Glade for which it is known that MLO genes can play a role in PM resistance. Only one of the four MLO genes found in rose has been functionally linked to powdery mildew resistance as transformation of *Rosa multiflora* "Baiyu" with antisense rhML01 provided plants with increased (but not absolute) resistance levels to powdery mildew (up to 15 days post inoculation) compared to the non-transgenic control plants.

Considering the above, there is a need in the art for further powdery mildew resistance providing genes.

It is an object of the present invention, amongst other objects, to meet the above need in the art.

According to the present invention, the above object, amongst other objects, is met by providing rose plants as outlined in the appended claims.

Specifically, the above object, amongst other objects, is met by providing rose plants being powdery mildew resistant and comprising in their nuclear genome at least one nucleotide sequence represented by SEQ ID No. 1 and at least one nucleotide sequence represented by SEQ ID No. 2 wherein the combined presence of SEQ ID No. 1 and SEQ ID No. 2 in said nuclear genome provides powdery mildew resistance.

The present inventors have surprisingly found that the combination of SEQ ID No. 1 and SEQ ID No. 2 provides a strong resistance to powdery mildew. According to the invention, it is essential that both resistance genes are combined because SEQ ID No. 1 provides in the absence of SEQ ID No. 2 no detectable powdery mildew resistance in rose while SEQ ID No. 2 provides in the absence of SEQ ID No. 1 minor powdery mildew resistance. The present inventors have further surprisingly discovered that the present resistance genes are dominant genes, i.e. the presence of a single copy of both genes suffices to provide powdery mildew resistance.

According to a preferred embodiment, the present invention relates to powdery mildew resistance against the ascomycete plant pathogen *Podosphaera pannosa* also known as *Sphaerotheca pannosa* var. *rosae*. In rose, the ascomycete plant pathogen *Podosphaera pannosa* is the major powdery mildew causing pathogen.

According to a further preferred embodiment, the present rose plants are *Rosa hybrida* plants and the present nuclear genome is a tetraploid genome. Especially in multiploid genomes such as diploid, triploid, tetraploid, hexaploid or octaploid genomes, the availability of dominant powdery mildew resistance genes provides a major advantage avoiding a multitude of intermediate powdery mildew phenotypes depending on the number of copies of the resistances genes present. The present multiploid genomes such as triploid, tetraploid, hexaploid or octaploid genomes can suitably directly be obtained or indirectly through genome doubling comprising SEQ ID Nos. 1 and 2. For example a tetraploid, hexaploid and octaploid can be readily obtained from a diploid genome comprising SEQ ID Nos. 1 and 2 and a hexaploid genome can also be obtained by genome doubling of a triploid plant.

According to still a further preferred embodiment, the present invention relates to powdery mildew resistant rose plants comprising in their nuclear genome at least one, preferably two, more preferably three, even more preferably four, nucleotide sequences represented by SEQ ID No. 1 such as 2, 3, 4, 5 or 6 in case of a hexaploid genome or such as 2, 3, 4, 5, 6, 7 or 8 in case of a octaploid genome and/or at least one, preferably two, more preferably three, even more preferably four, nucleotide sequences represented by SEQ ID No. 2, such as 2, 3, 4, 5 or 6 in case of a hexaploid genome or such as 2, 3, 4, 5, 6, 7 or 8 in case of a octaploid genome.

According to still a further preferred embodiment, the present invention relates to powdery mildew resistant rose plants comprising in their nuclear genome at least one, preferably three, more preferably four, nucleotide sequences, such as 2, 3, 4, 5 or 6 in case of a hexaploid genome or such as 2, 3, 4, 5, 6, 7 or 8 in case of a octaploid genome, represented by SEQ ID No. 1 or at least one, preferably two, more preferably three and even more preferably four, nucleotide sequences represented by SEQ ID No. 2 such as 2, 3, 4, 5 or 6 in case of a hexaploid genome or such as 2, 3, 4, 5, 6, 7 or 8 in case of a octaploid genome.

According to still a further preferred embodiment, the present invention relates to powdery mildew resistant rose plants comprising in their nuclear genome at least one, preferably two, more preferably three and even more preferably four nucleotide sequences represented by SEQ ID No. 1, such as 2, 3, 4, 5 or 6 in case of a hexaploid genome or such as 2, 3, 4, 5, 6, 7 or 8 in case of a octaploid genome and at least one, preferably two, more preferably three and eve more preferably four nucleotide sequences represented by SEQ ID No. 2, such as 2, 3, 4, 5 or 6 in case of a hexaploid genome or such as 2, 3, 4, 5, 6, 7 or 8 in case of a octaploid genome.

According to an especially preferred embodiment, the present powdery mildew resistant rose plants are selected from the group consisting of cut rose, pot rose, rose rootstock and garden rose, preferably cut rose.

According to yet another especially preferred embodiment, the present powdery mildew resistant rose plants exhibit a dominant phenotype.

Considering the beneficial properties of the above powdery mildew resistance provided by a synergistic epistatic effect between two dominant genes, the present invention further relates to methods for selecting a powdery mildew resistant rose plant as defined above, the method comprising the steps of:
a) isolating nuclear genomic DNA from a rose plant;
b) establishing the presence of SEQ ID No. 1 and SEQ ID No. 2 in the isolated nuclear genomic DNA;
c) establishing the powdery mildew phenotype of said rose plant wherein the presence of SEQ ID No. 1 and SEQ ID No. 2 indicates a powdery mildew resistant phenotype.

Figure 2:
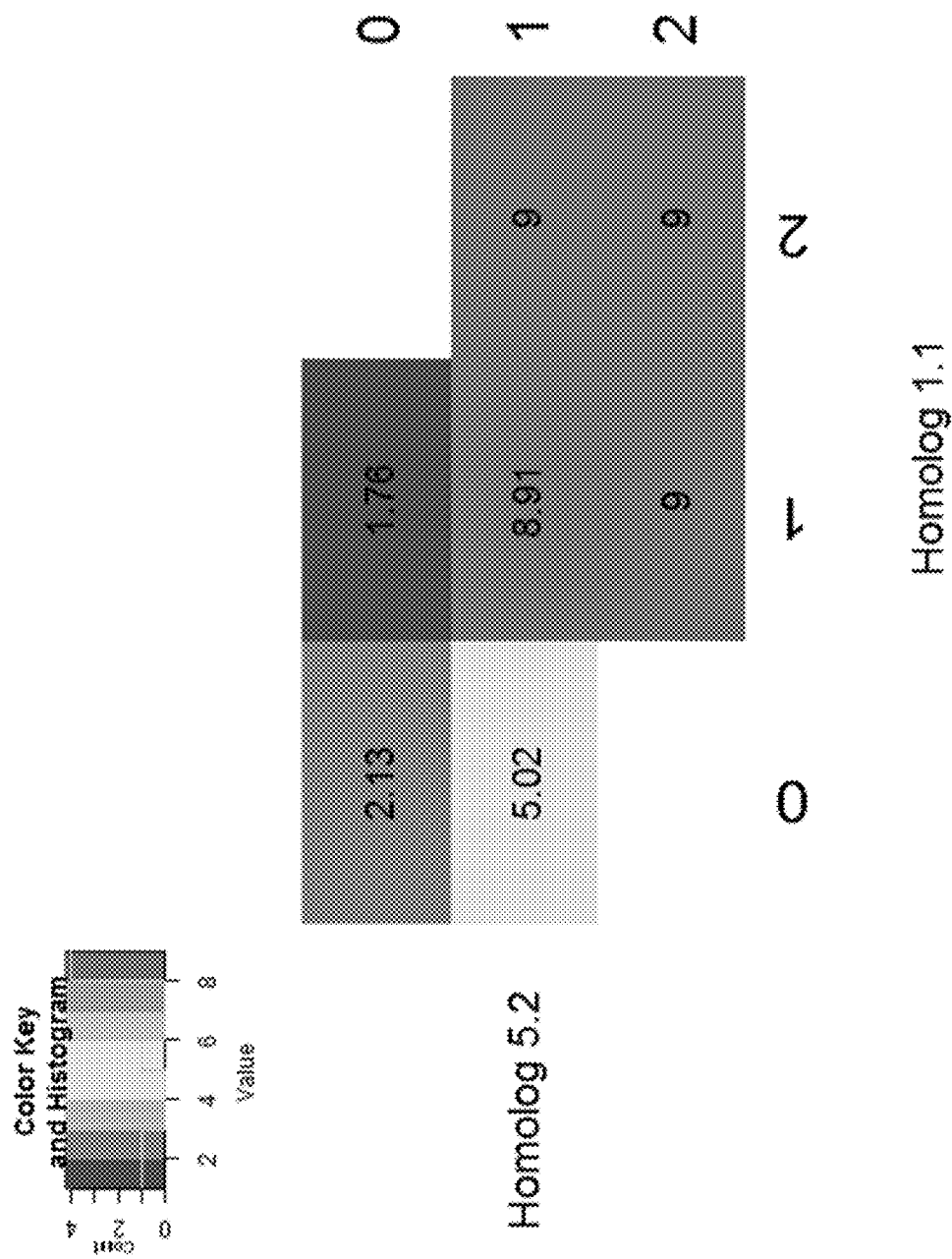

The present invention will be further detailed in the following example. In the examples, reference is made to figures wherein:

FIG. 1: shows a boxplot showing the effects of resistance alleles SEQ ID No. 1 and SEQ ID No. 2 separately and in tandem. Presence of the resistance allele is indicated by a "+" and absence of the resistance allele is shown by the "−" sign. Plants with both resistance alleles are highly resistant;

FIG. 2: shows the number of copies of SEQ ID No. 1 and SEQ ID No. 2 required to provide the present powdery mildew resistance in rose plants.

EXAMPLE

Introduction

Here, we investigated the number, effect sizes and genetic positions of QTL underlying PM resistance in a tetraploid F1 rose population (*Rosa hybrida*). We present our findings which show clear major effect QTL on linkage group 1 and linkage group 5 explaining 20% and 90% of the phenotypic variance in PM resistance respectively. We also show that the effect of the QTL is only seen when resistance alleles at both QTL are present as plants harbouring resistance alleles at both QTL are all highly resistant up until 15 weeks post-inoculation, whereas plants with only one or zero resistance alleles develop PM symptoms within this timeframe.

Method

A tetraploid F1 *Rosa hybrida* population was created by hand-pollinating the tetraploid cut rose RS-1183 ("Avalanche", hereafter named P1) with pollen from a tetraploid garden rose. Seeds of the tetraploid F1 *Rosa hybrid* population were deposited on Nov. 17, 2017 at National Collections of Industrial, Food, and Marine Bacteria (NCIMB), NCIMB Ltd. Ferguson Building Craibstone Estate, Bucksburn, Aberdeen, AB21 9YA Scotland according to the terms of the Budapest Treaty, with accession number NCIMB 42777. One of the resulting F1 offspring was self-pollinated to create an F2 population. The parents, 235 F1 offspring and 42 F2 plants were screened for resistance against PM (*Podosphaera pannosa*). The isolate was originally isolated from infected roses in a horticultural greenhouse, and the inoculum was obtained from a previous PM assay. Inoculation was performed in a block design, and six cuttings from each variety were randomized over 6 blocks. The bio-assay was carried out under long day conditions with temperature set at 20° C. and 23° C. for night and day respectively. Relative humidity alternated between 60% during the day and 85% at night. For each plant of the F1 population infection levels were scored 1, 3, 6, 9, 12 and 15 weeks post infection, for each plant of the F2 population infection levels were scored 6 and 12 weeks post infection, and infection levels of plants of both populations were scored on a scale between 1 and 9, where 1 represents the most susceptible individuals and 9 represents fully resistant individuals.

All plants were genotyped using the WagRhSNP Axiom SNP array. This chip contains 68,893 SNPs which are targeted by two probes from each direction. Quality control was performed using the R package FitPoly and 67,779 markers were retained for 51,685 SNPs. After removing SNPs with more than 5% missing data 42,143 markers remained. A total of 232 F1 individuals were successfully genotyped, of which 3 were removed as they were genetic outliers, and one because of missing phenotypic data. Further quality control was performed by checking the reproducibility of the genotypes of the parents, non-expected segregation, genotypic outliers, skewed markers and null alleles as well as differences between plates.

A previously obtained genetic map (using the K5 population) was used to map these correlated SNPs to linkage group (LG) and genetic position. All associated SNPs segregated following a scenario where the resistant parent was simplex and the susceptible parent was nulliplex. For chromosomes where QTL were found, linkage maps were constructed in JoinMap using markers that were simplex in P2 and nulliplex in P1, and QTL analyses was performed in MapQTL.

For each genomic region which was significantly associated with PM resistance, KASP primers were designed targeting the most significantly associated SNP as well as one SNP on either side. KASP primers were designed using the flanking sequences of the probes targeting the associated SNPs on the WagRhSNP Axiom SNP array.

Parents and a total of 48 randomly selected F1 plants were genotyped at all SNPs using KASP assays. Genotypes were scored as the number of resistance alleles harbored by an individual. As the resistant parent had one copy of the resistance allele at every associated SNP and the susceptible parent zero, genotype dosage in the F1 was limited to 0 (nulliplex for the resistance allele) and 1 (simplex for the resistance allele).

Results

A total of 267 markers had a correlation with PM resistance of >0.35. All highly correlated markers were found on linkage group 1 and 5 on the genetic map obtained using the K5 population. For markers that were included in our genetic map as well as the map obtained using the K5 population, order was conserved confirming that construction of the linkage map for these two linkage groups was successful.

Three weeks post inoculation, the SNP M23333_428 on homolog 5.2 explained up to 90% of phenotypic variance (LOD=114.2). A second SNP, G54183_559 was found 15 weeks post inoculation on LG1 on homolog 1.1 (LOD=23.1) at 60.5 cM, which explained 20.3% of the phenotypic variance. Analysing the QTL jointly using a Multiple QTL Model showed that the QTL on homologs 5.2 and 1.1 are needed for absolute resistance after 15 weeks. In total 86 plants with PM resistance data were genotyped using KASP assays, of which 48 were F1 offspring, 29 were F2 plants (the full-sib offspring of one selfed F1 plant) and 4 were P1 and P2 (including duplicates for both).

We first analyzed the association between SNP genotypes and PM resistance in the F1 population. Genotyping call rate varied between 87% (for G8670_490) and 100%. Looking at the association between KASP genotypes and PM resistance, the presence of resistance alleles at the most strongly associated SNPs on both homologs was strongly indicative of PM resistance 15 weeks post-inoculation. All plants with this combination of genotype showed a PM score greater than 8 (highly resistant, FIG. 1), whereas plants with resistant genotypes at one locus, or none at all, were never highly resistant and predominantly highly susceptible (FIG. 2). An analysis using ANOVA showed that the synergistic epistatic effect was strongly significant (Table 1). Further genomic analysis of the rose plants yielded SEQ ID Nos 1 and 2 directly related with the resistance genes underlying the present resistance.

TABLE 1

Parameter estimates for the effects of SEQ ID No.
1: TTTGTTCATTATAAACTCATTCCTCGCTTCCTCAACCTTCTCTGA
AACGACC) and SEQ ID No. 2: GG
CTTTTCGCCCTGCGTCTTGCTCTCCAAAAACTCACTACTAATTTGTCA
on powdery mildew resistance (15 weeks post-
inoculation) from a linear model. Positive
parameter estimates indicate that resistant
genotypes are more resistant than susceptible
genotypes. The positive interaction term
indicates a synergistic epistatic effect: the
effect of harboring a resistant genotype on one
homolog is stronger if a resistant genotype
the other homolog is also present.

| Variables | Parameter estimate | Standard error | P |
|---|---|---|---|
| Intercept | 2.02 | 0.42 | <0.0001 |
| SEQ ID No. 1 | 1.93 | 0.6 | 0.002 |

TABLE 1-continued

Parameter estimates for the effects of SEQ ID No.
1: TTTGTTCATTATAAACTCATTCCTCGCTTCCTCAACCTTCTCTGA
AACGACC) and SEQ ID No. 2: GG
CTTTTCGCCCTGCGTCTTGCTCTCCAAAAACTCACTACTAATTTGTCA
on powdery mildew resistance (15 weeks post-
inoculation) from a linear model. Positive
parameter estimates indicate that resistant
genotypes are more resistant than susceptible
genotypes. The positive interaction term
indicates a synergistic epistatic effect: the
effect of harboring a resistant genotype on one
homolog is stronger if a resistant genotype
the other homolog is also present.

| Variables | Parameter estimate | Standard error | P |
|---|---|---|---|
| SEQ ID No. 2 | -0.26 | 0.75 | 0.73 |
| Interaction between SEQ ID No. 1 and SEQ ID No. 2 | 5.18 | 0.99 | <0.0001 |

After showing that the presence of resistance genes at both loci is needed to confer resistance, we then examined whether the mode of action at each locus was fully dominant, in other words, there is no difference in PM resistance between plants having one resistance allele at each locus and plants that have multiple resistance alleles at each locus. To do this, we combined data from a F2 population with the data from the parents and F1 population. The F2 populations was a selfed population obtained by selfing a F1 plant with 1 resistance allele at each locus, thus, assuming polysomic inheritance we expect plants with 0, 1 and 2 copies at each locus in the resulting dataset. PM resistance in the F2 population was only assayed until 12 weeks post-inoculation. PM resistance 12-weeks post-inoculation was strongly correlated with PM resistance 15 weeks post-inoculation (r=0.98), meaning that restricting our analyses to 12 weeks post-inoculation data does not meaningfully affect our conclusions.

And indeed, it was clearly shown that one resistance allele at each locus is enough to confer absolute resistance 12 weeks post-inoculation, and the presence of multiple resistance genes per locus does not confer meaningfully additional resistance (FIG. 2) which is clear evidence that resistance alleles are dominant over susceptible alleles.

The invention claimed is:

1. A powdery mildew resistant *Rosa hybrida* plant comprising in its nuclear genome at least one nucleotide sequence having the sequence of SEQ ID NO: 1 and at least one nucleotide sequence having the sequence of SEQ ID NO: 2, wherein the combined presence of SEQ ID NO: 1 and SEQ ID NO: 2 in said nuclear genome provides powdery mildew resistance, and wherein a representative sample of seed of said powdery mildew resistant *Rosa hybrida* plant was deposited under accession number NCIMB 42777.

2. The powdery mildew resistant *Rosa hybrida* plant according to claim 1, wherein said powdery mildew resistance is a resistance against the ascomycete plant pathogen *Podosphaera pannosa*.

3. The powdery mildew resistant *Rosa hybrida* plant according to claim 1, wherein said nuclear genome is a tetraploid genome, a hexaploid genome, an octaploid genome, or a diploid genome.

4. The powdery mildew resistant *Rosa hybrida* plant according to claim 1, comprising in its nuclear genome at least two nucleotide sequences having the sequence of SEQ ID NO: 1 and/or at least two nucleotide sequences having the sequence of SEQ ID NO: 2.

5. The powdery mildew resistant *Rosa hybrida* plant according to claim 3, comprising in its nuclear genome at least three nucleotide sequences having the sequence of SEQ ID NO: 1 and/or at least three nucleotide sequences having the sequence of SEQ ID NO: 2.

6. The powdery mildew resistant *Rosa hybrida* plant according to claim 3, comprising in its nuclear genome at least four nucleotide sequences having the sequence of SEQ ID NO: 1 and/or at least four nucleotide sequences having the sequence of SEQ ID NO: 2.

7. The powdery mildew resistant *Rosa hybrida* plant according to claim 1, wherein said *Rosa hybrida* plant is selected from the group consisting of cut rose, pot rose, garden rose, and rose rootstock.

8. The powdery mildew resistant *Rosa hybrida* plant according to claim 1, wherein said powdery mildew resistance is a dominant resistance.

9. A method for selecting a powdery mildew resistant *Rosa hybrida* plant according to claim 1, the method comprising the steps of:
  a) isolating nuclear genomic DNA from a *Rosa hybrida* plant;
  b) establishing the presence of SEQ ID NO: 1 and SEQ ID NO: 2 in the isolated nuclear genome DNA; and
  c) establishing the powdery mildew phenotype of said *Rosa hybrida* plant, wherein the presence of SEQ ID NO: 1 and SEQ ID NO: 2 indicates a powdery mildew resistant phenotype.

* * * * *